(12) United States Patent
Pletnev

(10) Patent No.: US 10,850,114 B2
(45) Date of Patent: Dec. 1, 2020

(54) DISTRIBUTED MAGNETIC THERAPEUTIC INDUCTOR

(71) Applicant: Sergey Pletnev, Minsk (BY)

(72) Inventor: Sergey Pletnev, Minsk (BY)

( * ) Notice: Subject to any disclaimer, the term of this patent is extended or adjusted under 35 U.S.C. 154(b) by 125 days.

(21) Appl. No.: 15/569,088

(22) PCT Filed: Apr. 25, 2016

(86) PCT No.: PCT/IB2016/052329
§ 371 (c)(1),
(2) Date: Oct. 25, 2017

(87) PCT Pub. No.: WO2016/174563
PCT Pub. Date: Nov. 3, 2016

(65) Prior Publication Data
US 2018/0117351 A1    May 3, 2018

(30) Foreign Application Priority Data
Apr. 25, 2016 (EA) ................... 201500717

(51) Int. Cl.
*A61N 2/02* (2006.01)
(52) U.S. Cl.
CPC .................. *A61N 2/02* (2013.01)
(58) Field of Classification Search
CPC .............. A61N 2/02; A61N 2/00–12
See application file for complete search history.

(56) References Cited

U.S. PATENT DOCUMENTS

| | | | |
|---|---|---|---|
| 6,500,110 B1 * | 12/2002 | Davey | A61N 2/02 128/DIG. 25 |
| 2005/0154249 A1 | 7/2005 | Ardizzone | |
| 2016/0220838 A1 * | 8/2016 | Scheinowitz | A61N 2/02 |

FOREIGN PATENT DOCUMENTS

| | | |
|---|---|---|
| RU | 7009 U1 | 7/1998 |
| RU | 15963 U1 | 11/2000 |
| RU | 2007128243 A | 1/2009 |
| RU | 114622 U1 | 4/2012 |

OTHER PUBLICATIONS

ISR; Federal Institute of Industrial Property; Moscow, Russia; July 5, 2016.

* cited by examiner

*Primary Examiner* — Thaddeus B Cox
(74) *Attorney, Agent, or Firm* — Patshegen IP LLC; Moshe Pinchas

(57) ABSTRACT

This invention relates to a distributed magnetic therapeutic inductor comprising multiple planar electromagnetic inductors arranged within a flat flexible mat and inducing the electromagnetic field perpendicular to the mat plane. The inductor is characterized in that a magnetically conductive surface closing magnetic circuits of the inductors to each other is made on the back side of the mat. Magnetically conductive surface is made in the form of a flexible magnetically conductive layer arranged exteriorly on the mat surface.

5 Claims, 1 Drawing Sheet

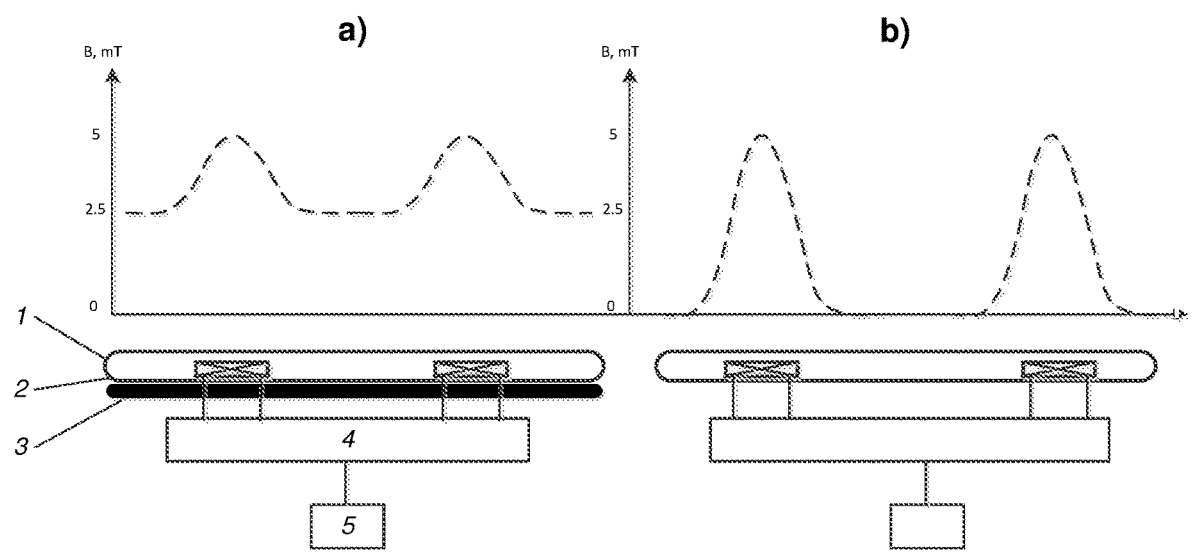

DISTRIBUTED MAGNETIC THERAPEUTIC INDUCTOR

The invention relates to the field of magnetotherapy, in particular, to the structures of distributed magnetic inductors configured for a comprehensive therapeutic treatment.

Matrasses with distributed permanent magnets built into a layer of a flexible material are known from the prior art, for example, they are disclosed in U.S. Pat. No. 7,081,083.

These matrasses are used for the relaxation magnetotherapy, however, they are characterized by low efficacy of treatment and habituation effect.

Matrasses with distributed built-in electromagnetic inductors are known from the prior art, for example, they are disclosed in Patent CN1060035. Alternating or pulsed magnetic field is induced in these inductors connected either in series or via switches depending on the selection of an area of exposure, synchronous exposure or on the traveling wave technique.

Therapeutic efficacy of these inductors is significantly higher, however the effect of each inductor is localized and covers exclusively the areas arranged opposite the inductors. In such a case, adjacent regions and organs are not exposed to the magnetic field. In addition, these inductors are too energy-intensive and require a steady external power supply.

The objective of the invention is to improve both biological efficacy of the pulsed electromagnetic field therapy and energy efficiency.

The objective of the invention is achieved as described as follows: the electromagnetic field in the distributed magnetic therapeutic inductor comprising multiple planar electromagnetic inductors arranged within a mat is induced perpendicular to the mat plane, in addition, a magnetically conductive surface closing magnetic circuits of the inductors to each other is made on the back side of the mat. In such a case, a volume-surface pulsed magnetic field is induced on the upper side of the mat across the entire length thereof.

A further improvement resides in the fact that the magnetically conductive surface is made in the form of a flexible magnetically conductive layer arranged externally on the mat surface. Forming the magnetically conductive surface in this manner allows flexibility of the mat to be maintained and the mat to be used for wrapping around the body or individual parts thereof. As a result, efficacy of the therapeutic treatment further increases.

It has been found in the process of measuring magnetic induction across the surface facing a patient that distribution of the magnetic field in conventional inductors is mainly concentrated opposite built-in inductors.

It has been found in the provided structure that the total level of magnetic induction across the entire working surface substantially increases when the magnetically conductive layer is used on the opposite side of the mat. In this case, the total volume of the operating magnetic field increases multifold and a substantially greater volume of tissues and organs in the region adjacent to the distributed inductor is exposed to the pulsed magnetic field.

It should be noted that if the mat and the magnetically conductive layer are made flexible, the body or parts thereof may be wrapped therewith, thereby still further improving treatment efficacy.

FIGS. 1a) and b) shows components of the structures of a distributed zo inductor according to the invention—a) and of a conventional design—b).

The diagrams of the longitudinal magnetic induction distribution V in mT in the near-surface volume are shown above these components. This distribution demonstrates the increase in effective volume of the pulsed magnetic field exposure.

Flexibility of the magnetically conductive layer may be achieved by distributing a ferromagnetic material within a layer of flexible polymer or the above layer may be made from multilayer steel foil.

The most effective magnetically conductive layer may be made from foil or film comprising a high magnetic permeability material, for example, metallic glass, NanoPerm, μu-metal, permalloy, electrical steel, Ni-Zn ferrite, Mn-Z ferrite, steel, $Fe_{49}Co_{49}V2$, Fe3% Si, $Fe67CoigBi_4Sii$, NisoFeso permalloy, Fe73.3Sii3.5Nb3B9Cu fine structure and Supermalloy.

In the embodiment there was used a standard IAMV5 matrass-type inductor of the "Unispok" magnetotherapeutic apparatus, having generator of pulses 5 connected to commutator 4 of distributed inductors in the form of planar coils 2 built into a porous polymer matrix 1. The magnetic induction at the surface of the inductor was 5 mT. Measurement of the longitudinal magnetic induction distribution demonstrated availability of isolated peaks at the inductor arrangement sites.

A steel plate 3 is disposed on a back side of the matrass.

Measurement of the longitudinal distribution demonstrated generation of the volume-surface pulsed magnetic field with induction of 2-2.5 mT and between peaks in the spaces between inductors. This resulted in formation of the distributed magnetic inductor with volume-surface distribution of the magnetic field that substantially improves therapeutic efficacy of this inductor due to more extensive volumetric effect on biological tissues.

At the same time, energy efficiency of inducing this field also increases. For example, at a 50 W rated power consumption of this inductor, power generator 5 consumption could be reduced to 5 W. This allows the use of less powerful energy sources, reduction in overall dimensions thereof, simplification of the structure of pulsed magnetic field-inducing devices and reduction in the total mass of therapeutic apparatuses.

Possibility emerges to produce self-contained therapeutic apparatuses to be used in a complex environment, for example, in the outer space, at home and while traveling. It should be noted that using high magnetic permeability materials may result in further optimization of the equipment.

The invention claimed is:

1. A distributed magnetic therapeutic inductor comprising multiple planar electromagnetic inductors arranged within a flat and flexible mat and inducing a magnetic field perpendicular to a mat plane, wherein said mat defines a front side and a back side and said magnetic field is induced on said front side and wherein a magnetically conductive layer closing magnetic circuits of the inductors to each other is made on said back side of the mat.

2. Inductor as claimed in claim 1, characterized in that the magnetically conductive layer is made in a form of a flexible magnetically conductive layer arranged exteriorly on surface of said mat.

3. Inductor as claimed in claim 1, characterized in that the magnetically conductive layer is made from a ferromagnetic material distributed in a layer of the mat.

4. Inductor as claimed in claim 1, characterized in that the magnetically conductive layer is made from multilayer ferromagnetic foil.

5. Inductor as claimed in claim 1, characterized in that the magnetically conductive layer is made from a metallic glass layer.

\* \* \* \* \*